(12) United States Patent
Zhang et al.

(10) Patent No.: US 7,309,786 B2
(45) Date of Patent: Dec. 18, 2007

(54) OLIGONUCLEOTIDE ANTAGONIST FOR HUMAN TUMOR NECROSIS FACTOR α (TNF-α)

(75) Inventors: Zhiqing Zhang, Beijing (CN); Xinrui Yan, Beijing (CN); Ketai Guo, Beijing (CN); Chunxiao Xu, Beijing (CN)

(73) Assignees: Institute for Viral Disease Control and Prevention, Beijing (CN); Chinese Center for Disease Control and Prevention, Beijing (CN)

( * ) Notice: Subject to any disclaimer, the term of this patent is extended or adjusted under 35 U.S.C. 154(b) by 124 days.

(21) Appl. No.: 10/822,761

(22) Filed: Apr. 13, 2004

(65) Prior Publication Data

US 2004/0254139 A1  Dec. 16, 2004

(30) Foreign Application Priority Data

May 15, 2003  (CN) ............................... 03 1 36113
Aug. 4, 2003  (CN) ............................... 03 1 49656

(51) Int. Cl.
*A61K 31/70* (2006.01)
*C07H 21/02* (2006.01)
*C07H 21/04* (2006.01)
*C12Q 1/68* (2006.01)

(52) U.S. Cl. ................... 536/24.5; 536/23.1; 536/24.1; 435/6; 514/44

(58) Field of Classification Search ..................... None
See application file for complete search history.

(56) References Cited

U.S. PATENT DOCUMENTS 6,346,398 B1 * 2/2002 Pavco et al. ............. 435/91.31
2004/0146890 A1 * 7/2004 Matsuzaki et al. ............. 435/6

* cited by examiner

*Primary Examiner*—Sean McGarry
(74) *Attorney, Agent, or Firm*—Birch, Stewart, Kolasch & Birch, LLP

(57) ABSTRACT

The present invention relates to a group of new oligonucleotides sequences with human tumor necrosis factor α (TNF-α) inhibiting activity, which includes DNA sequences and RNA sequences. These oligonucleotides or aptamer can specifically be bound to TNF-α and inhibit the cytoxicity of TNF-α to L929 cells. Therefore, the aptamer of the present invention may be used to detect TNF-α and provide a therapeutic method for diseases related to the increasing level of TNF-α. Compared with other TNF antagonists such as monoclonal antibody and soluble receptor, the present invention has high specificity, high affinity, quick penetration to target tissue, rapid plasma clearance, and lower immunogenecity. Turthermore, it can be used repeatedly and keeps high concentration in target tissue and the like. It has the advantages of affinity and specificity similar to monoclonal antibodies and also has permeability and pharmacokinetics characteristics similar to small molecular polypeptide. The present invention also refers to derivative of the oligonucleotides sequence, including modified sequence. The present invention may further be manufactured as medicine for therapy and diagnosis of TNF-α related diseases.

3 Claims, 8 Drawing Sheets

Negative control  $10^{-6}$ug  $10^{-5}$ug  $10^{-4}$ug  $10^{-3}$ug  $10^{-2}$ug  $10^{-1}$ug  Positive control Normal control    Aptamer treated    untreated Normal control    Aptamer treated    untreated

SEQUENCE LISTING

```
<160> NUMBER OF SEQ ID NOS: 33

<210> SEQ ID NO 1
<211> LENGTH: 40
<212> TYPE: DNA
<213> ORGANISM: Homo sapiens

<400> SEQUENCE: 1
cgcgcgtaaa tcttcttctg ttaccctctc ttcatgtcgc                              40

<210> SEQ ID NO 2
<211> LENGTH: 40
```

```
<212> TYPE: DNA
<213> ORGANISM: Homo sapiens

<400> SEQUENCE: 2
cgctggagga cgatgttaat tagaccgcaa ctacattgca                              40

<210> SEQ ID NO 3
<211> LENGTH: 40
<212> TYPE: DNA
<213> ORGANISM: Homo sapiens

<400> SEQUENCE: 3
cgatctacgt ggtgactcat acgtgtcgat gtgcctttcc                              40

<210> SEQ ID NO 4
<211> LENGTH: 40
<212> TYPE: DNA
<213> ORGANISM: Homo sapiens

<400> SEQUENCE: 4
gcacactaag tttctacacg tctcgtcgcc ctctttgtgc                              40

<210> SEQ ID NO 5
<211> LENGTH: 40
<212> TYPE: DNA
<213> ORGANISM: Homo sapiens

<400> SEQUENCE: 5
atggcgcagt cggcgacaat cactttggtt actattggcc                              40

<210> SEQ ID NO 6
<211> LENGTH: 40
<212> TYPE: DNA
<213> ORGANISM: Homo sapiens

<400> SEQUENCE: 6
cggtgtcccg gcactttgat cgtcgacctg ttgtattgcc                              40

<210> SEQ ID NO 7
<211> LENGTH: 40
<212> TYPE: DNA
<213> ORGANISM: Homo sapiens

<400> SEQUENCE: 7
ggcggggtct ctaaagtgtg ttatcatctg cttgttggcc                              40

<210> SEQ ID NO 8
<211> LENGTH: 40
<212> TYPE: DNA
<213> ORGANISM: Homo sapiens

<400> SEQUENCE: 8
cactgtaatc agaggctttt ttactctcgc tgcattccgg                              40

<210> SEQ ID NO 9
<211> LENGTH: 40
<212> TYPE: DNA
<213> ORGANISM: Homo sapiens

<400> SEQUENCE: 9
gcccagcgtc cgacactaac tagtcgccaa acaatcagcc                              40
```

```
<210> SEQ ID NO 10
<211> LENGTH: 40
<212> TYPE: DNA
<213> ORGANISM: Homo sapiens

<400> SEQUENCE: 10
tggcgagtat actcacaaac ctctcacagg aacctggggc                              40

<210> SEQ ID NO 11
<211> LENGTH: 40
<212> TYPE: DNA
<213> ORGANISM: Homo sapiens

<400> SEQUENCE: 11
tgcacaccgg tgatttagcc tggcgtgctt caccttcacc                              40

<210> SEQ ID NO 12
<211> LENGTH: 40
<212> TYPE: DNA
<213> ORGANISM: Homo sapiens

<400> SEQUENCE: 12
ccacgtctac acttacccct gtgacagcta tactcatcac                              40

<210> SEQ ID NO 13
<211> LENGTH: 40
<212> TYPE: DNA
<213> ORGANISM: Homo sapiens

<400> SEQUENCE: 13
ccccgccatg tgcttagtgc aataacgttc tcaccgcccc                              40

<210> SEQ ID NO 14
<211> LENGTH: 40
<212> TYPE: DNA
<213> ORGANISM: Homo sapiens

<400> SEQUENCE: 14
cactgtttga cgtttcggat taaggagtcc gctcgcaccc                              40

<210> SEQ ID NO 15
<211> LENGTH: 40
<212> TYPE: DNA
<213> ORGANISM: Homo sapiens

<400> SEQUENCE: 15
tcccatcaaa accaaatttc gggtctgctc tctctctgcc                              40

<210> SEQ ID NO 16
<211> LENGTH: 40
<212> TYPE: DNA
<213> ORGANISM: Homo sapiens

<400> SEQUENCE: 16
tggggatgcg gtctgcctaa caacagggct tcacttaccc                              40

<210> SEQ ID NO 17
<211> LENGTH: 40
<212> TYPE: DNA
<213> ORGANISM: Homo sapiens

<400> SEQUENCE: 17
ccgacgtact cggtagacaa gtcccctgaa gtgtgacgcc                              40
```

```
<210> SEQ ID NO 18
<211> LENGTH: 40
<212> TYPE: DNA
<213> ORGANISM: Homo sapiens

<400> SEQUENCE: 18
gcggccgata aggtctttcc aagcgaacga attgaaccgc                          40

<210> SEQ ID NO 19
<211> LENGTH: 40
<212> TYPE: RNA
<213> ORGANISM: Homo sapiens

<400> SEQUENCE: 19
ccccggguuc uguaugaucc gaccggucag auaagaccac                          40

<210> SEQ ID NO 20
<211> LENGTH: 41
<212> TYPE: RNA
<213> ORGANISM: Homo sapiens

<400> SEQUENCE: 20
ucaucggugu gugaguuagc ucacgugccg uuucgaaggc g                        41

<210> SEQ ID NO 21
<211> LENGTH: 40
<212> TYPE: RNA
<213> ORGANISM: Homo sapiens

<400> SEQUENCE: 21
cgugcuagau gcuacgagug gucuccucac guagaagggg                          40

<210> SEQ ID NO 22
<211> LENGTH: 40
<212> TYPE: RNA
<213> ORGANISM: Homo sapiens

<400> SEQUENCE: 22
cguuguagua guggcuugggcauaacucag uuaaacacua                           40

<210> SEQ ID NO 23
<211> LENGTH: 40
<212> TYPE: RNA
<213> ORGANISM: Homo sapiens

<400> SEQUENCE: 23
cgcaucguuu gcguggcgug uccgggcgcc gauucguaaa                          40

<210> SEQ ID NO 24
<211> LENGTH: 40
<212> TYPE: RNA
<213> ORGANISM: Homo sapiens

<400> SEQUENCE: 24
aggacguacu uggaaaagag gcgcgaagaa ccugguaugu                          40

<210> SEQ ID NO 25
<211> LENGTH: 40
<212> TYPE: RNA
<213> ORGANISM: Homo sapiens

<400> SEQUENCE: 25
caagccgagg gggaguaucu gaugacaauu cggagcucca                          40
```

<210> SEQ ID NO 26
<211> LENGTH: 39
<212> TYPE: RNA
<213> ORGANISM: Homo sapiens

<400> SEQUENCE: 26
cguauauacg gauuagguug uagcucagac caguaaugu                                      39

<210> SEQ ID NO 27
<211> LENGTH: 40
<212> TYPE: RNA
<213> ORGANISM: Homo sapiens

<400> SEQUENCE: 27
caugggcuag accggcauaa aacugcugua guugcacgcc                                     40

<210> SEQ ID NO 28
<211> LENGTH: 40
<212> TYPE: RNA
<213> ORGANISM: Homo sapiens

<400> SEQUENCE: 28
ggucccacau agguuggucu uguuguaugg gcuguuugca                                     40

<210> SEQ ID NO 29
<211> LENGTH: 71
<212> TYPE: DNA
<213> ORGANISM: Artificial Sequence
<220> FEATURE:
<223> OTHER INFORMATION: Description of artificial sequence: synthetic
      oligonucleotide primer
<220> FEATURE:
<221> NAME/KEY: misc_feature
<222> LOCATION: (16)..(55)
<223> OTHER INFORMATION: n is a, c, g, or t

<400> SEQUENCE: 29
gggaggacga tgttannnnn nnnnnnnnnn nnnnnnnnnn nnnnnnnnnn nnnnnaagaa              60
gactcgcaag a                                                                   71

<210> SEQ ID NO 30
<211> LENGTH: 15
<212> TYPE: DNA
<213> ORGANISM: Artificial Sequence
<220> FEATURE:
<223> OTHER INFORMATION: Description of artificial sequence: synthetic
      oligonucleotide primer

<400> SEQUENCE: 30
gggaggacga tgtta                                                               15

<210> SEQ ID NO 31
<211> LENGTH: 16
<212> TYPE: DNA
<213> ORGANISM: Artificial Sequence
<220> FEATURE:
<223> OTHER INFORMATION: Description of artificial sequence: synthetic
      oligonucleotide primer

<400> SEQUENCE: 31
tcttgcgagt cttctt                                                              16

<210> SEQ ID NO 32
<211> LENGTH: 17
<212> TYPE: DNA
<213> ORGANISM: Artificial Sequence

```
-continued

<220> FEATURE:
<223> OTHER INFORMATION: Description of artificial sequence: synthetic
      oligonucleotide primer

<400> SEQUENCE: 32
taatacgact cactata                                                  17

<210> SEQ ID NO 33
<211> LENGTH: 32
<212> TYPE: DNA
<213> ORGANISM: Artificial Sequence
<220> FEATURE:
<223> OTHER INFORMATION: Description of artificial sequence: synthetic
      oligonucleotide primer

<400> SEQUENCE: 33
taatacgact cactataggg aggacgatgt ta                                 32
```

OLIGONUCLEOTIDE ANTAGONIST FOR HUMAN TUMOR NECROSIS FACTOR α (TNF-α)

This Non-provisional application claims priority under 35 U.S.C. § 119(a) on Patent Application No(s). 03136113.7 and 03149656.3 filed in China on May 15, 2003 and Aug. 4, 2003, respectively, the entire contents of which are hereby incorporated by reference.

FIELD OF THE INVENTION

The present invention refers to a group of new oligonucleotides sequences, in particular, a new group of oligonucleotides with inhibiting activity against human tumor necrosis factor α (TNF-α). The target oligonucleotides or aptamer specifically bound to TNF-α was selected from a random oligonucleotides library by SELEX technique. The present invention further relates to derivative sequence, including modified sequences, and the application of the oligonucleotides to manufacture for diagnosis or treatment of the diseases related to TNF-α.

BACKGROUND OF THE INVENTION

The human tumor necrosis factor α (hTNF-α) is a multifunctional cytokine secreted by macrophage/monocyte and has wide spectrum of biological activity. It plays important roles in inflammatory reaction, immune regulation, tumor suppression, anti-microorganism and helminth infection. It also plays a central role in cytokine network. When suffering from inflammation, autoimmune disease, allergy, shock, the expression of TNF-α increases by hundreds of thousands to develop inflammation process and exacerbatethe disease. As TNF-α is an important virulence factor, it is closely involved in many autoimmune diseases, e.g., rheumatoid arthritis (RA), children multiple rheumatoid arthritis (JRA), pyremia, cardiac infarction, systemic lupus erythematosus (SLE) and diabetes. Therefore, antagonist of TNF-α is important for the treatment of these diseases ("Tumor Necrosis Factor Receptor Family Members in the Immune System", *Immunology*, 1998, 10:423~434).

There are many TNF blockade for the treatment of the diseases mentioned above (referring to "Treatment of Rheumatoid Arthritis: New Therapeutic Approaches with Biological Agents", *Curr Durg Targets Immune Endocr Metabol Disord*, 2001 May; 1 (1): 45-65). For example, Infliximid, (Avakine; ReMicade) manufactured by Johnson & Johnson Ltd., U.S.A. for treating rheumatoid arthritis, and Crohn's disease has already been available in market since November 1998. Infliximide is a chimeric antibody against hTNF-α. The Etemercept (Embrel; Enbrel) for treating rheumatoid arthritis and Crohn's disease, manufactured by Immunex Ltd., U.S.A. has already been available in market since December 1998. Etemercept is a fusion protein of the IgG1 Fc domain and the TNF receptor p75 (Etanerecept in rheumatoid arthritis. Expert Opin Pharmacother, 2001, 2(7): 1137~1148) (Psoriatic Arthritis: The Role of TNF Inhibition and The Effect of its Inhibition with Etanercept. Clin Exp Rheumatol. 2002 November-December; 20(6 Supple 28): S116-21). Although these protein drugs provide good therapeutic effect, there are still disadvantages. First, the process of protein preparation is complicated and expensive; secondly, the protein drug has high molecular weight, very difficult to get to the target tissues because of its poor permeability; thirdly, the blood clearance is so low that it is difficult to excrete, which results in its accumulation in the body and causes side effect; finally, due to the introduction of the exogenous proteins and the change of structure, the proteins have immunogenicity, once repeatedly used, it induces antibody formation. The polypeptide with low molecular weight has good pharmacokinetic characteristics and strong capability of tissue permeability, however, the target molecule is unavailable and the molecule has low affinity, which limits the clinical application (referring to "What Are the Risks of Biologic Therapy in Rheumatoid Arthritis? An Update on Safety by J. Rheumatol, Suppl. 2002 September; 65:33-8).

DESCRIPTION

To overcome the problem of the prior art, we have screened out a group of oligonucleotides sequences being able to specifically bind to TNF, including DNA sequences (Nos. 1~18) and RNA sequences (Nos. 19~28). The group of oligonucleotides sequences is selected from a) oligonucleotides showed in SEQ No. 1;
b) oligonucleotides showed in SEQ No. 2;
c) oligonucleotides showed in SEQ No. 3;
d) oligonucleotides showed in SEQ No. 4;
e) oligonucleotides showed in SEQ No. 5;
f) oligonucleotides showed in SEQ No. 6;
g) oligonucleotides showed in SEQ No. 7;
h) oligonucleotides showed in SEQ No.8;
i) oligonucleotides showed in SEQ No.9;
j) oligonucleotides showed in SEQ No.10;
k) oligonucleotides showed in SEQ No.11;
l) oligonucleotides showed in SEQ No.12;
m) oligonucleotides showed in SEQ No.13;
n) oligonucleotides showed in SEQ No.14;
o) oligonucleotides showed in SEQ No.15;
p) oligonucleotides showed in SEQ No.16;
q) oligonucleotides showed in SEQ No.17;
r) oligonucleotides showed in SEQ No.18;
s) oligonucleotides showed in SEQ No.19;
t) oligonucleotides showed in SEQ No.20;
u) oligonucleotides showed in SEQ No.21;
v) oligonucleotides showed in SEQ No.22;
w) oligonucleotides showed in SEQ No.23;
x) oligonucleotides showed in SEQ No.24;
y) oligonucleotides showed in SEQ No.25;
z) oligonucleotides showed in SEQ No.26;
aa) oligonucleotides showed in SEQ No.27; and
bb) oligonucleotides showed in SEQ No.28.

Wherein, the sequences Nos. 1-18 are DNA sequences with secondary structures typified by structure I (for SEQ ID NO: 1) and structure II (for SEQ ID NO: 5) as shown below:

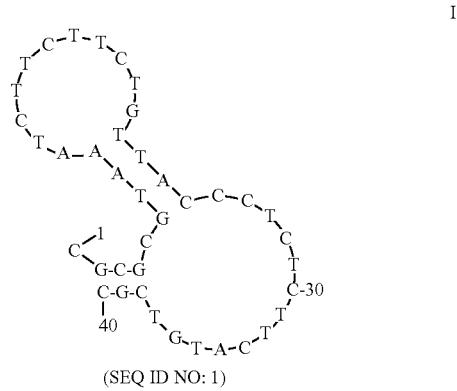

(SEQ ID NO: 1)

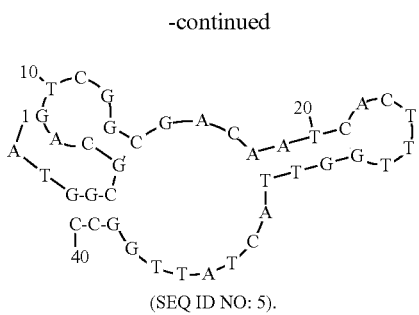

(SEQ ID NO: 5).

The sequences Nos. 19-28 are RNA sequences with secondary structures typified by structure III (for SEQ ID NO: 19) and structure IV (for SEQ ID NO: 25) as shown below:

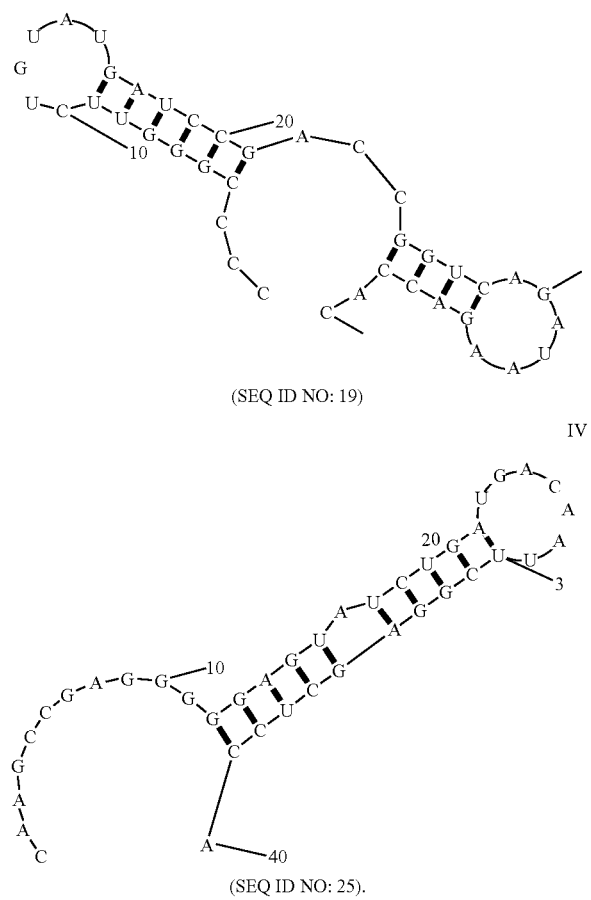

(SEQ ID NO: 19)

(SEQ ID NO: 25).

The oligonucleotide sequence in accordance to the present invention further includes a homologues oligonucleotide sequence that is at least 80% homologues to and functions identical to the oligonucleotide sequence.

The oligonucleotide sequence in accordance to the present invention further includes a truncated oligonucleotide sequence that functions identical or similar to the oligonucleotide sequence.

The oligonucleotide sequence in accordance to the present invention further includes a modified oligonucleotide sequence that functions identical to the oligonucleotide sequence.

The oligonucleotide sequence in accordance to the present invention further includes a hybridization oligonucleotide sequence that is hybridized with the oligonucleotide sequence under strict condition.

The oligonucleotide sequence in accordance to the present invention further includes a derived oligonucleotide sequence that is derived from the oligonucleotide sequence.

The application of the oligonucleotide sequence in accordance with the present invention to prepare the drugs for diagnosis or therapy of diseases related to TNF-α.

The oligonucleotides or aptamers in accordance with the present invention are selected by SELEX technique, which may be a single-stranded RNA, a single-stranded DNA, or a double-stranded DNA. The aptamers can be specifically bound to the target molecules and inhibit their biological effects. Compared with the protein antagonist, the aptamers have advantages of high specificity and affinity, quick penetration to target tissue, rapid plasma clearance, excretion from kidney, and low immunogenicity. The aptamers may be used in vivo repeatedly and maintained high concentration in target tissue. Oligonucleotides can be prepared in vitro and is convenient to be prepared and purified. They do not interact with other protein or antigen and are not prone to induce individual immune response. In addition to those advantages mentioned above, aptamers can be specifically modified in large scale for research and clinical application. Aptamers can be labeled with fluorescent dye, radioactive isotope, and biotin for research purpose. It can also be bound to radioactive nucleotide, cytotoxin, and other toxin in clinical application.

All the protein epitopes are suitable target sites of aptamers. The dissociation constant of the oligonucleotides selected by SELEX technique used as antagonists is 50 pM-10 nM, which is the same as the binding affinity between target molecule and receptor. As a result, oligonucleotides can compete with receptor in binding to target molecules.

The affinity between aptamers and target molecules is higher than that of ScFv and short peptide expressed by bacteriophage with their target molecules. The molecular weight of aptamers is 8-15 KD, which is between polypeptide (1 KD) and ScFv (25 KD), while the molecular weight of dimeric aptamers is similar to ScFv's.

The oligonucleotides, namely aptamers as mentioned above, can effectively inhibit the cytotoxicity of TNF-α on L929 cells, which shows that aptamers can effectively inhibit the binding of TNF-α to its receptor. Consequently, the aptamers of the present invention can be used to cure the diseases related to increasing TNF-α. The permeability and pharmacokinetics characteristics of aptamers are similar to the macromolecule polypeptide.

EMBODIMENTS OF THE INVENTION

Figure 1:
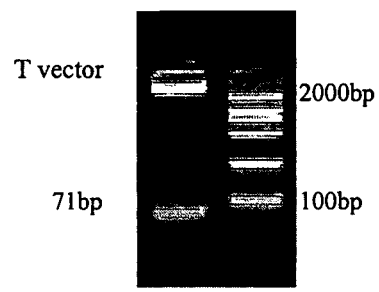
FIG. 1 shows the results of electrophoresis of the PCR product from SELEX product, the size of which is about 71 bp.

The following examples are presented to further illustrate the present invention. It is not intended that the present invention be limited in scope by reason of any of the following examples. One skilled in this art should understand that these examples could be modified and varied without deviating from it. These modification and verification should be covered by attached claims.

SELEX technique was employed in selecting oligonucleotide aptamers in the present invention. The term "SELEX" refers to systematic evolution of ligands by exponential enrichment. Single-stranded oligonucleotides have the diversity characteristic both in molecular structure and function, thus, a random library of the single-oligonuleotides is synthesized for binding to the target protein on the membrane. The oligonuleotides bound non-specifically is washed away and then, the oligonuleotides bound specifically was eluted in denatured condition and collected. The oligonuleotides are amplified by PCR for further selection. The high affinity oligonucleotides, namely aptamers that have high affinity with the target proteins, can be selected from the initial library through amplification and selection for many times. In 1990, Tuerk and Gold selected Aptamers of T4 RNA polymerase by SELEX (systematic evolution of ligands by exponential enrichment: RNA Ligands to Bacteriophage T4 DNA Polymerase, Tuerk C. Gold L. Science. Vol. 249, 505-510, 1990). Subsequently, Ellington and Szostak showed great interests in the application of aptamers in scientific research and production. Aptamers soon become a valuable research tool and show great application prospected in the fundamental research, drug selection and clinical diagnosis and therapy (In vitro selection of RNA molecules that bind specific ligands. Nature. 1990 Aug. 30; 346 (6287): 818-22). At present, many kinds of aptamers have come into clinical test phase. For example, drugs are useful for curing cruor and thrombus and inhibiting endometrium hyperplasic and angiogenesis ("*Nucleases-resistant Nucleic Acid Ligands to Vascular Permeability Factor/Vascular Endothelial Growth Factor*", Chem Biol. 1995 October; 2(10): 683-95; "*Oligonucleotide Inhibitors of Human Thrombin that Bind Distinct Epitomes*", J. Mol. Biol. 1997 October 10; 272(5): 688-98; "*Inhibition of Receptor Binding and VEGF-induced Vascular Permeability Through Interactions Requiring the Exon 7-encoded Domain*" J. Biol. Chem, 1998 Aug. 7;273(32):20556-67).

The single-stranded DNA random library and primers used in SELEX were synthesized by Da Lian Takara Company. Both ends were fixed sequences, 40 bp random sequence in the middle: 5'-ggg agg acg atg tta(N40)aag aag act cgc aag a-3'(SEQ ID NO: 29), library capacity is $10^{15}$-$10^{16}$, primer 1: 5'-ggg agg acg atg tta-3'(SEQ ID NO: 30), primer 2: 5'-tct tgc gag tct tct t-3'(SEQ ID NO: 31), primer 3: 5'-taa tac gac tca cta α-3' (SEQ ID NO: 32), primer 4: 5'-taa tac gac tca cta ta ggg agg acg atg tta-3' (SEQ ID NO: 33). TNF-α was prepared in our laboratory, and T4 In vitro Transcription Kit was purchased from Promega. MLV reverse transcription enzyme was bought from Biolab. Cellulose Nitrate and Acetic filter membrane was bought from Millipore. Oligonucleotides purified reagent were purchased from Qiagen. T vector was bought from Promega. Other reagents were bought from some big reagent companies. The followings were the technical routes for identification and characterization of oligonucleotides.

In accordance with the present invention, a ssDNA oligonucleotide random library is synthesized→an oligonucleotides library is selected by SELEX→the oligonucleotide bound specifically to TNF is amplified→next selection is carried out→a target oligonucleotide sequence is acquired after selection for 12~15 cycles→the sequence is cloned and analyzed→the binding activity to TNF is detected→the biological activity is detected.

Examples 1-4 shown below were carried out to select and identify the DNA aptamers and detect their biological activity.

Examples 5-18 shown below were carried out to select and identify the RNA aptamers and detect their biological activity.

Examples 19-21 shown below were carried out to evaluate the in vivo efficacy of RNA aptamer in rat adjuvant arthritis model.

EXAMPLE 1

Select Aptamers Bound Specifically to TNF in Vitro

Amplify DNA library

The single-stranded DNA library was amplified with primer 1 and primer 2 and then, 1 μl of single-stranded DNA product was used for asymmetric PCR amplification. The product was recycled and then, 200 µl binding buffer (2×1M Nacl, 40 mM Tris Cl, 2 mM MgCl2) was added. After 5 min denatured at 95° C. and 5 min cooled on ice bath, 1 µl TNF (1 g/µl) was added and incubation of 1 hour at 37° C. was taken, followed with filtration. After washed with PBS, the product was soaked in 300 µl wash buffer (10 mM EDTA, 7M Urea binding buffer), and DNA precipitated with ethanol. A next round of selection was performed with 10 µl of the obtained solution as template. In last selections, high affinity oligonucleotides were obtained with less TNF. In total, 12 cycles of selection were made.

Clone and Sequence

After 12 cycles of selection, the selected product was bound to PGEM-T vectors (Promega). 18 aptamers (the target oligonucleotides sequence) were obtained after testifying by PCR and sequence. FIG. 1 shows the PCR results. The sequences of the 18 aptamers oligonucleotides are showed in SEQ ID Nos. 1-18.

EXAMPLE 2

Analysis of Secondary Structure of Aptamers

The lowest energy of the secondary structure and the structures of the 18 aptamers was analyzed and simulated by DNASYS v2.5 software, which showed at least two kinds of specific secondary structure existed. The model I illustrates one structure, which has characteristic of double stem-loop structure (SEQ ID NO: 1). Another structure is illustrated in model II, which has characteristic tertiary stem-loop structure (SEQ ID NO: 5).

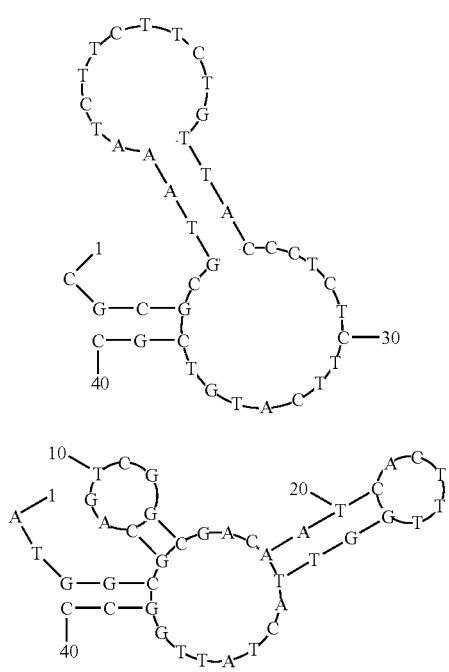

EXAMPLE 3

Evaluating Affinity of DNA Aptamers with TNF

The affinity of synthesized DNA aptamers, which were labeled by biotin, with TNF were assayed by two methods.

Figure 2:
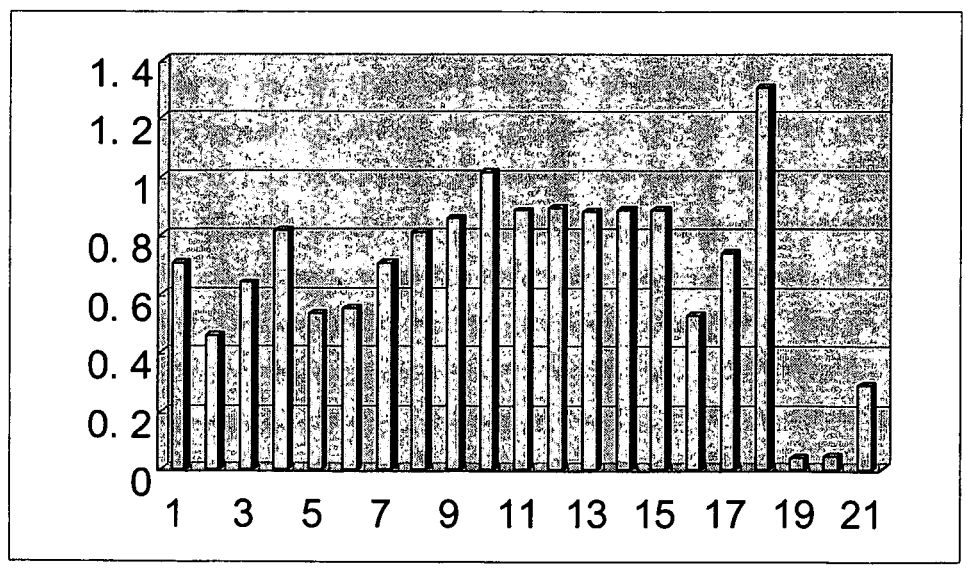
FIG. 2 shows the affinity of aptamers with TNF by ELISA; ordinate is OD450 value, abscissal-18 represents 18 selected aptamers, 19 is the blank control, 20 is negative control 1 (untreated with nucleic acid), and 21 is negative control 2 (primary oligonucleotides library)

Routine ELISA: 96-well polystyrene plate was coated with 1 µg/ml TNF and blocked for 2 h with 3% BSA at 37° C.; two times serial-diluted 5' biotin-labeled DNA aptamers were added into each well and incubated for 1 hour at 37° C.; 100 µl Peroxidase Horseradish-labeled streptavidin at a dilution of 1 in 400 was added into the wells and was incubated for 1 hour at 37° C.; and DAB in the dark was added. The OD450 value was read by microplate reader. FIG. 2 shows the results.

Figure 3:
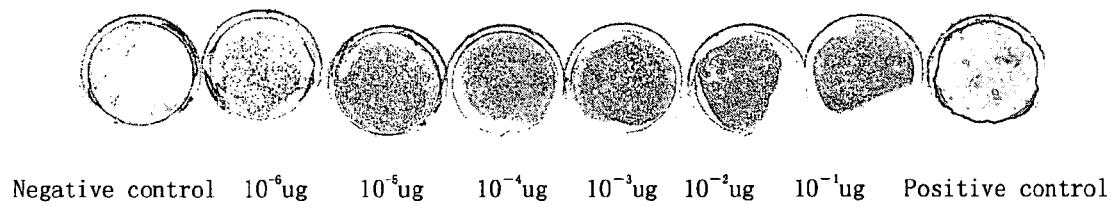
FIG. 3 shows the affinity of aptamers with TNF by Dot-ELISA; the color intensity did not increase any more when the ssDNA was 4 μg, while no color intensity was detected when the ssDNA was less than $10^{-6}$ μg.

Dot-ELISA: 5'-biotin-labeled nucleic acids of different concentrations was mixed with TNF and incubated in water bath for 1 h at 37° C.; the NC membrane was fixed in the filter and filtrated the mixture; the unbound nucleic acids was washed away, peroxidase horseradish-labeled streptavidin was added to the membrane and incubation was taken for 30 min at 37° C.; and then, DAB was added. FIG. 3 shows the results. The color intensity did not increase any more when the ssDNA was 4 µg, while the color intensity did not occurred once the ssDNA was less than 10-6 µg.

The above results indicate that the binding of the DNA aptamers to TNF is specific and has high affinity.

EXAMPLE 4

Measurement Detection of Aptamers Anti-TNF Activity

Figure 4:
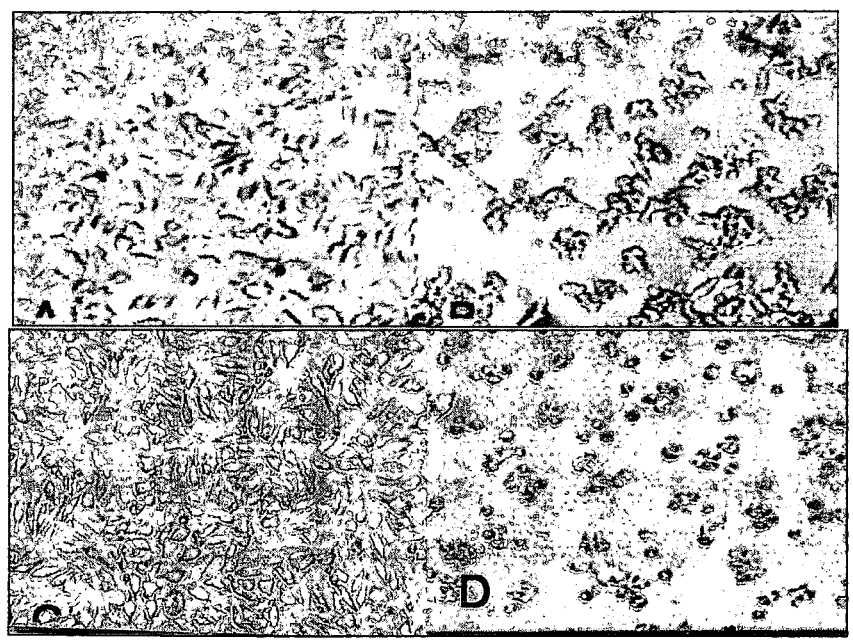
FIG. 4 shows the L929 cells in different growth conditions; (1) L929 cells in normal condition; (2) L929 cells killed 50% by TNF; (3) L929 cells added with mixture of nucleic acid-TNF; and (3) L929 cells killed 100% by TNF.

Mouse L929 cells were cultured in 96-well culture plates. Mixture of 1 µg/ml Mitomycin, TNF, and oligonucleotides of different concentrations were added into each well. The live/dead cell proportion was observed after 24 hours culture. The cell viability was measured by MTT assay. Results are shown in FIG. 4. A: L929 cells grown in normal condition; B: 50% of the total cells were killed by TNF; C: L929 cells added with mixture of nucleic acid-TNF; and D: 100% of the total cells were killed by TNF. The results demonstrate that the selected nucleic acid aptamers could inhibit the killing effect of the TNF to L929 cells.

The following are the examples of selecting TNF-specific-binding RNA aptamers by SELEX technique.

EXAMPLE 5

Obtain Double-Stranded DNA Library

The single-stranded DNA library was amplified with primer 2: 5'-tct tgc gag tct tct t-3'(SEQ ID NO: 31), primer 3: 5'-taa tac gac tca cta α-3'(SEQ ID NO: 32) and primer 4: 5'-taa tac gac tca cta ta ggg agg acg atg tta-3'(SEQ ID NO: 33), and then the amplified products were purified with Nucleic acid Purification Kit (Qiagen).

EXAMPLE 6

Obtaining Single-Stranded RNA Library by In Vitro Transcription 1 nmol DNA template, the buffer, T7 RNA polymerase, and Rnase inhibitor were mixed and incubated for 1 hour at 37° C.; 1 µl RQ1 Dnase was added and then, incubated for 15 min at 37° C.; transcriptions were purified with Nucleic acid Purification Kit (Qiagen); PAGE (polyacrylamidedel electrophoresis) was carried out. The result shows that in vitro transcriptions with 71 bases were obtained.

EXAMPLE 7

Obtaining TNF-binding Oligonucleotides from Single-Stranded RNA Library 1 nmol ssRNA was denatured for 5 min at 95° C. and incubated on ice for 5 min; 180 µl binding buffer (1 mM MgCl2, 10 mM DTT in PBS) and 200 pmol TNF were added and incubated for 30 min at 37° C., followed filtration; a membrane was washed with PBS, put into the centrifuge tube, and soaked in 300 µl elution buffer (10 mM EDTA, 7M urea binding buffer); RNA was precipitated with ethanol; the RNA product was amplified by RT-PCR to get the double-stranded DNA. The products were processed in vitro transcription after amplification and used in the next round of selection. In the last rounds of selection, a little TNF was added to get oligonucleotides of high affinity with TNF. In total, 12 rounds of selection were made.

EXAMPLE 8

Evaluatiing the Affinity of TNF with RNA Aptamers Obtained from Each Round Selection by ELISA In vitro transcription was processed with the RT-PCR product obtained from each round of selection and then, the products were labeled with biotin-labeled UTP (a mixture of labeled UTP and unlabeled UTP 1 in 2); the wells of the microplate were coated with 50 µl TNF (1 µg/ml) and incubated overnight at 4° C.; blocked with 100 µl 1% BSA and incubated for 1 hours at 37° C., 50 µl biotin-labeled RNA was added and incubated for 1 hour at 37° C.; incubation was washed and TMB and H2O2 were added.

Figure 5:
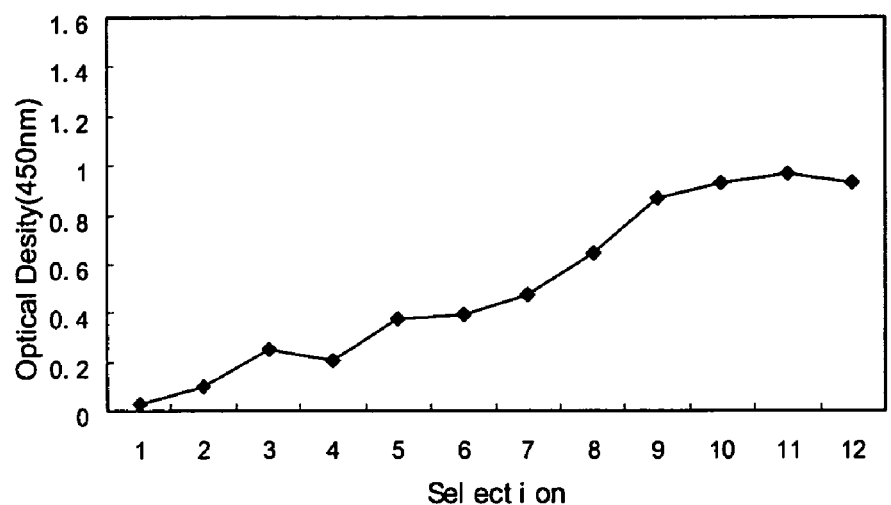
FIG. 5 shows the affinity of RNA aptamers selected from 1 to 12 rounds with TNF.

50 µl diluted Horseradish Peroxidase conjugated streptavidin was added to each well and incubated for 1 hour at 37° C., a substrate was added, after developing at room temperature for 10 min, the plate was read at 450 nm wavelength. FIG. 5 shows the results. With more rounds of the selection, the binding activity of the aptamers to TNF rises. After the 12th round of selection, binding activity does not increase.

EXAMPLE 9

Cloning and Sequencing Target Oligonucleotides

The double-strand DNA gotten from the product of the 12th round selection amplified by RT-PCR is combined with pMEG-T vector and then the vector was transferred into *E. coli* DH5α; the white colonies were pick out, plasmid was extracted and the positive clones were determined; the double-strand DNA was amplified with the positive clone as the template and then, ssRNA was obtained by in vitro transcription; the binding ability of ssRNA to TNF-α was determined by dot blot; the positive clone was picked out and sequenced. Results are showed in SEQ ID Nos. 19-28. 10 sequences with high affinity to TNF-α were obtained with.

EXAMPLE 10

Analyzing Secondary Structure of RNA Aptamers

Two representative secondary structures as shown below were obtained using RNA structure analysis software.

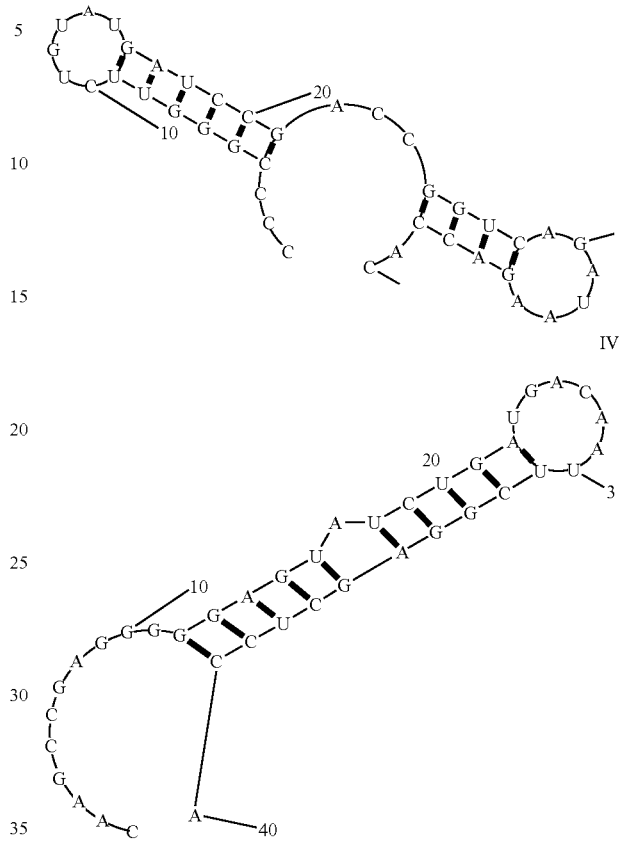

Taking structure III as example, the major character is 5' or 3' single or double stem-loop structure (SEQ ID NO: 19); the other example is structure IV, which character is tertiary stem-loop structure (SEQ ID NO: 25).

EXAMPLE 11

Figure 6:
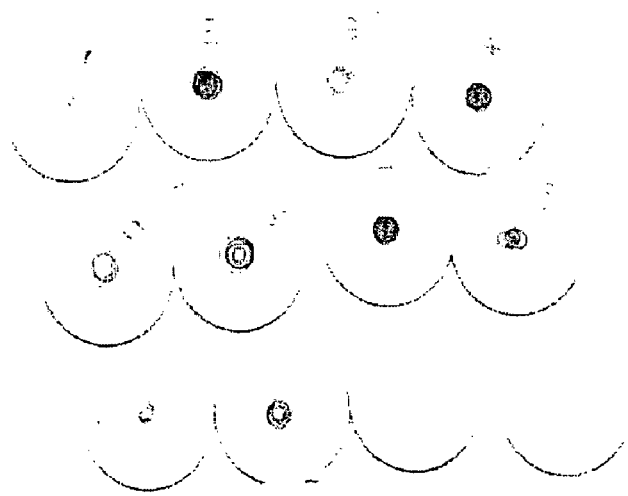
FIG. 6 shows the affinity of RNA aptamers with TNF by Dot-blot; RNA binds to TNF, in which Nos.1~10 are 10 RNA sequences being selected, No. 11 is primary library; No. 12 is negative control (untreated with TNF-α)

Evaluating Affinity of Oligonucleotides with TNF-α by Dot Blot Hybridization The oligonecleotides were obtained after 12 rounds of selection. The corresponding oligo-DNA were synthesized and transcribed with biotin labeled UTP and NTP to the oligo-RNA; 10ng biotin-labeled RNA and 100 ng TNF-α were added into 20 ul binding buffer and then, incubated for 30 min at 37° C.; the sample was spotted onto the cellulose membrane and then blocked with 2% BSA for 1 hour at 37° C.; HRP-labeled avidin was added and then diaminobenzidine (DAB) at last. Results are showed in FIG. 6 that demonstrates the 10 RNA aptamers bind to TNF-α to different content, while as the affinity of original RNA library with TNF-α is very low.

EXAMPLE 12

Detecting the Binding Activity of Aptamers to TNF by Gel-Shift Assay 40 bases oligo-RNA obtained from in vitro transcription were denatured as in example 11 for 5 min at 95° C. and then, quickly incubated for 5 min on ice bath; 10 µl binding buffer and 0.2 µl TNF were added and incubated for 30 min at 37° C. in the water bath; the sample was loaded into 5% PAGE, silver staining was carried out and the result was observed. Because RNA 1-10 binds to TNF, the band of the aptamers was retarded. RNA library does not bind to TNF-α, and there is no gel shift.

EXAMPLE 13

Evaluating Binding Affinity of RNA Aptamers to TNF-α by ELISA

Figure 7:
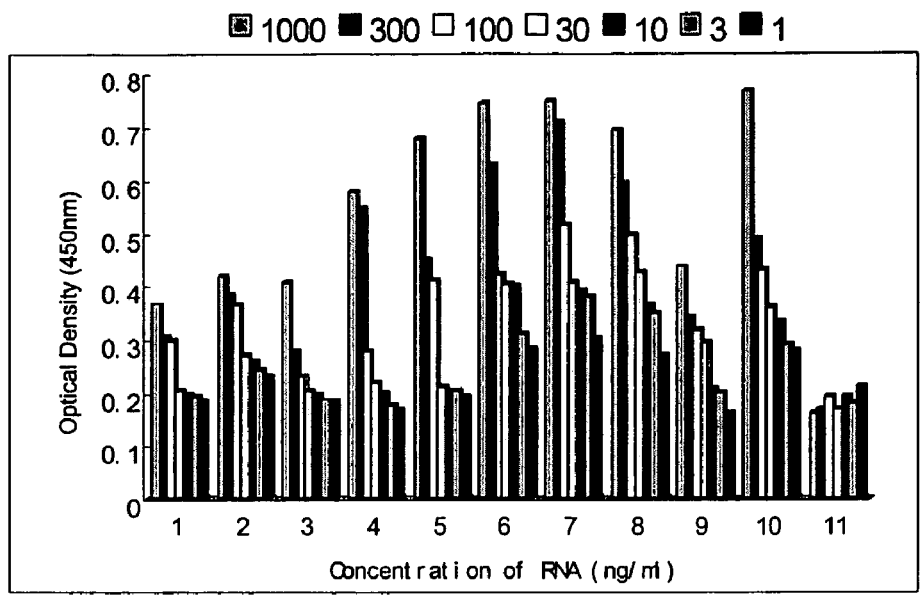
FIG. 7 shows the results of selected RNA binding to TNF-α by ELISA; Nos. 1~10 are 10 RNA sequences and No. 11 is RNA library.

The oligo-RNA obtained from in vitro transcription was serially diluted and then the binding activity of oligo-RNA to TNF-α was evaluated by ELISA. FIG. 7 shows the results. 10 RNA aptamers bind to TNF-α to different content, in which 5, 6, 7, 8, and 10 bind to TNF-α with higher affinity. Also, the result is still positive when the concentration is 3 nm/ml. The RNA library does not bind to TNF-α.

EXAMPLE 14

Figure 8:
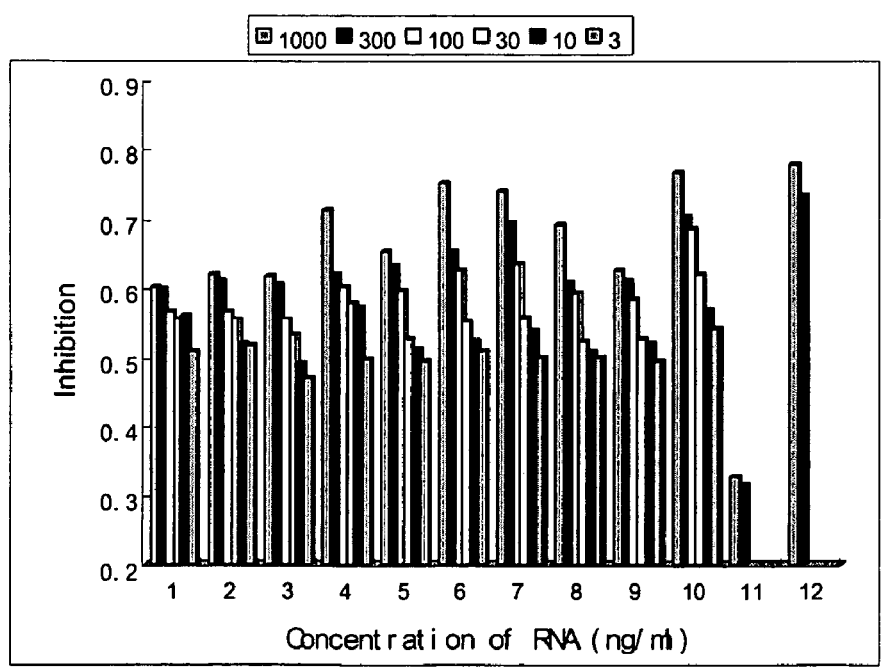
FIG. 8 shows inhibitory effect on 10 unit hTNF-α-mediated cytotoxicity in L929 cells by oligonucleotides in serial dilution; Nos. 1~10 are 10 RNA sequences being selected, No. 11 is premier library, and No.12 are normal cells.

Inhibition of hTNF-αMmediated Cytoxicity 100 ng RNA aptamers obtained from in vitro transcription was diluted serially with RPMI1640 culture medium containing 10% FBS and 1 µg/ml Mitomycin, hTNF-α was added with a final concentration of 10 unit and incubated for 2 hour at 37° C.; the biological activity of the remnants in vitro of hTNF-α was measured with mouse L929 cells; stained with MTT, the OD value was determined at 570 nm. FIG. 8 shows inhibitory effect on 10 units hTNF-α-mediated cytoxicity in L929 cells by oligonucleotides in serial dilution and has dosage relation. 10 pM sample can still protect 50% of cells.

EXAMPLE 15

Truncated Oligonucleotides Aptamers

In order to reduce the cost of chemistry synthesized aptamers, the selected oligonucleotides aptamers were truncated on the basis of preserving high affinity. Four aptamers SEQ No. 20, 23, 25, and 26, which have better binding activity and biological activity, were picked out and truncated to 30 bp. The stem-loop structures pertinent to biological function were remained, and the following sequences are obtained:

```
The shortened of SEQ No. 20: GCUUAGCAAACGCACCGCACAGGCCCGCGG.

The shortened of SEQ No. 23: CACUCAAUCG AGUGCACGGCAAAGCUUCCG.

The shortened of SEQ No. 25: CCUCAUAGAC UACUGUUAAG CCUCGAGG.

The shortened of SEQ No. 25: AUGCCUAAUC CAACAUCGAG UCUGGUCAU.
```

Figure 9:
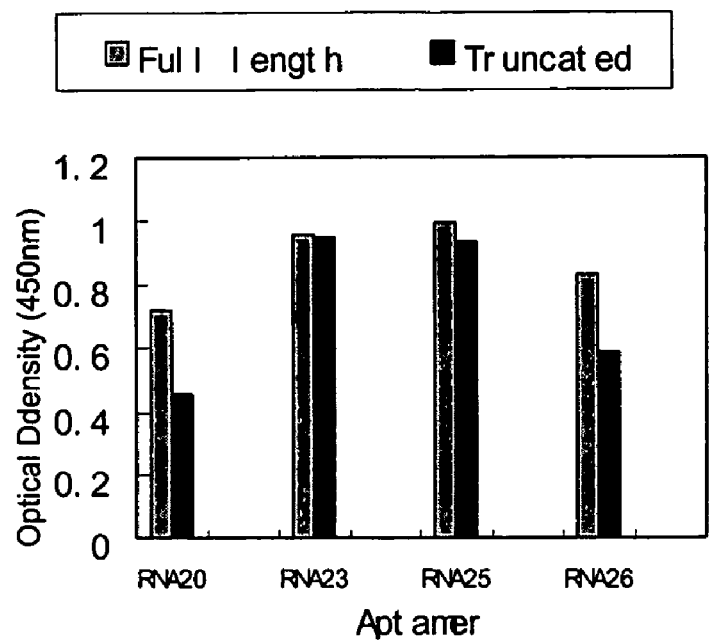
FIG. 9 shows the binding activity of the truncated RNA aptamers to TNF-α by ELISA; Nos. 1~2 are original and truncated sequences of SEQ No. 20 respectively, Nos. 3~4 are from SEQ No. 23, Nos. 5~6 are from SEQ No. 25, and Nos. 7~8 are from SEQ No. 26.

The binding activity of the truncated RNA aptamers to TNF-α was measured by ELISA. The results are showed in FIG. 9. Nos. 1~2 are the original and the truncated sequences of SEQ No. 20 respectively, Nos. 3~4 that of SEQ No. 23, Nos. 5~6 that of SEQ No. 25, and Nos. 7~8 that of SEQ No. 26. The results show that the affinity of the truncated aptamers changes somewhat, two of which, SEQ No. 20 and SEQ No. 25, decrease slightly, while the other of which, SEQ No. 23 and SEQ No. 26, decrease obviously compared with the original aptamers.

EXAMPLE 16

Chemical Modification of Oligonucleotides Aptamers

Figure 10:
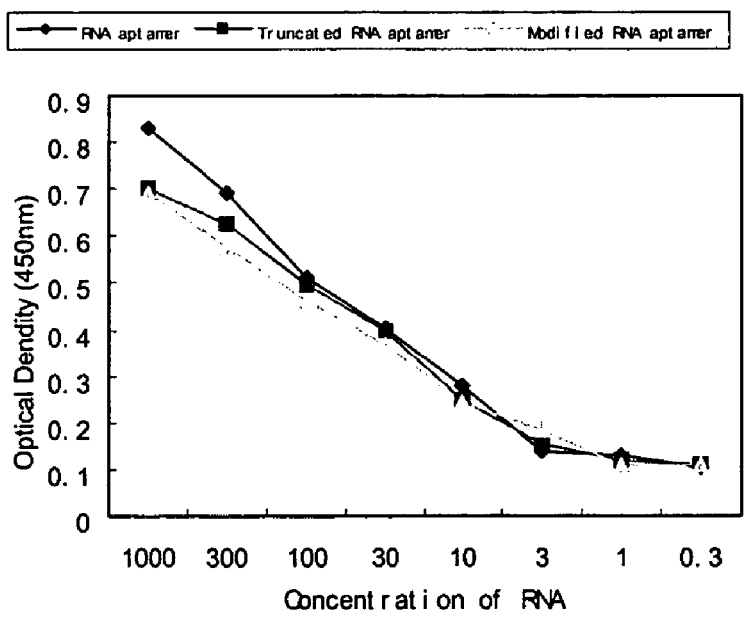
FIG. 10 shows the binding affinity of RNA aptamers truncated and modified from RNA aptamers SEQ No. 25.

Chemical modification can increase the stability and biological utilization of oligonucleotides aptamers. Modification is an experiential process. After each modification, the oligonucleotides aptamers' affinity and inhibition activity should be measured. The pyrimidine bases of 4 original RNA aptamers were modified with 2-fluorin and 2-amido and were truncated, and then the affinity and inhibition activity was measured. The measure method is the same as that described in examples 13 and 14. FIG. 10 shows the results, demonstrating that the affinity and inhibition activity of RNA aptamers truncated and modified from RNA aptamers SEQ Nos. 20 and 25 remains unchanged.

Figure 11:
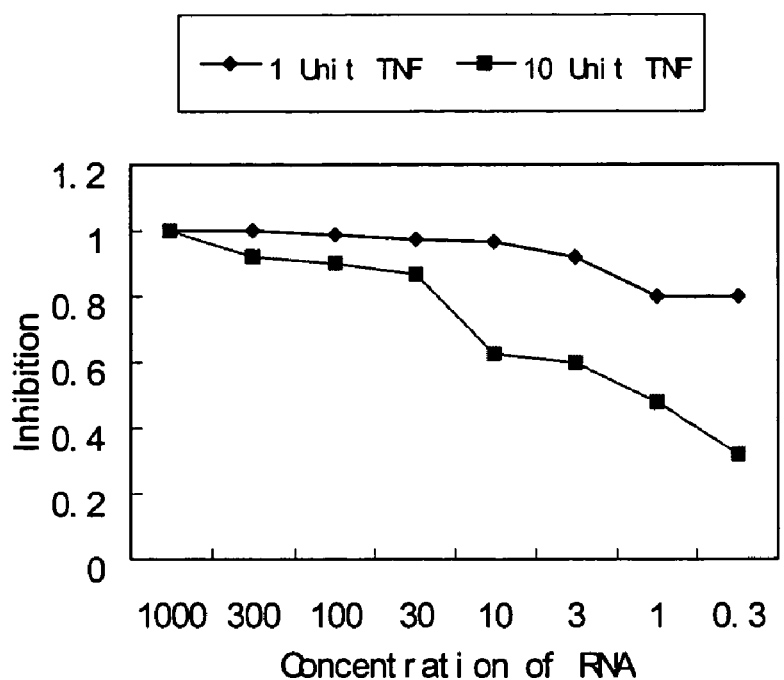
FIG. 11 shows the protection of L929 cells by RNA SEQ No. 25 in different dilution concentration against TNF-α; the TNF is 1 unit and 10 units, respectively.

The affinity activity of the truncated and modified RNA aptamers was measured using ELISA. FIG. 10 shows the result. When the concentration is 3 ng/ml, there is still positive result and apparent dosage relation. The three curves represent RNA aptamers SEQ No. 25, truncated SEQ No. 25 aptamers, amino-modified aptamers, respectively. It shows that the binding affnity of the truncated and modified aptamers keeps unchanged. Further experiment shows that the modified aptamers have the same ability as the original aptamers to inhibit the activity of TNF. It was determined that the inhibitory effect on hTNF-α-mediated cytoxicity in L929 cells was remained. FIG. 11 shows the result. When adding 1 Unit TNF, 10 ng/ml sample can protect the cells from being destroyed and there is obvious dosage relation.

EXAMPLE 17

Figure 12:
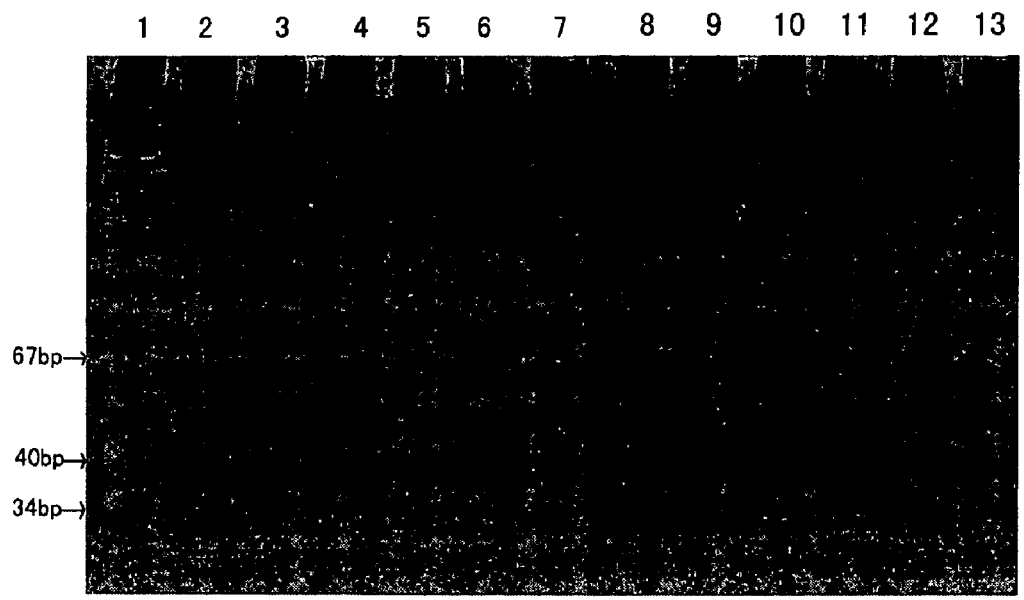
FIG. 12 shows the result of RNA SEQ No. 25 degraded in 85% mouse serum with PAGE; No. 1 is a DNA marker, Nos. 2-7 are modified aptamers digested for 0, 1, 2, 4, 8, and 16 hours respectively, Nos. 8-13 are unmodified aptamers digested for 0, 1, 2, 4, 8, and 16 hours respectively.

Stability Test of RNA Aaptamers in Serum 500 ng unmodified and amino-modified RNA aptamers SEQ No. 25 were taken out and 200 µl un-inactivated fresh human serum was added respectively. PBS was added until the overall volume is 240 µl. They were mixed and incubated in water bath at 37° C. 40 ul mixture samples were taken out and digested for 0 h, 1 h, 2 h, 4 h, 8 h, and 16 h, respectively. The hydroxybenzene and chloroform were used for extraction and then 10 µl of the extract to carry out PAGE was taken out. The silver staining was processed and the result was observed. FIG. 12 shows the result. No. 1 is DNA marker, Nos. 2-7 are modified aptamers digested respectively for 0 h, 1 h, 2 h, 4 h, 8 h, and 16 h, Nos. 8-13 are unmodified aptamers digested respectively for 0 h, 1 h, 2 h, 4 h, 8 h, and 16 h. The results show that amino-modified RNA aptamers have good stability. The half-life of the aptamers in serum is about 8 hours.

EXAMPLE 18

Degradation Test 250 ng RNA aptamers SEQ No. 25 was taken out and then RNase was added to a final concentration of 20 µg/ml, followed incubation in water bath at 37° C. 20 µl sample was taken out after reaction for different time. Hydroxybenzene and chloroform were added to extract the samples. After purification the silver staining was performed and the result was observed. The results show that the RNA degradation completely after reacting for 1 hour, which demonstrates that the RNA cannot stand the digestion of RNase with a high concentration and testifies that is surely RNA molecule.

EXAMPLE 19

In Vivo Study on Rat Arthritis Model

Figure 13:
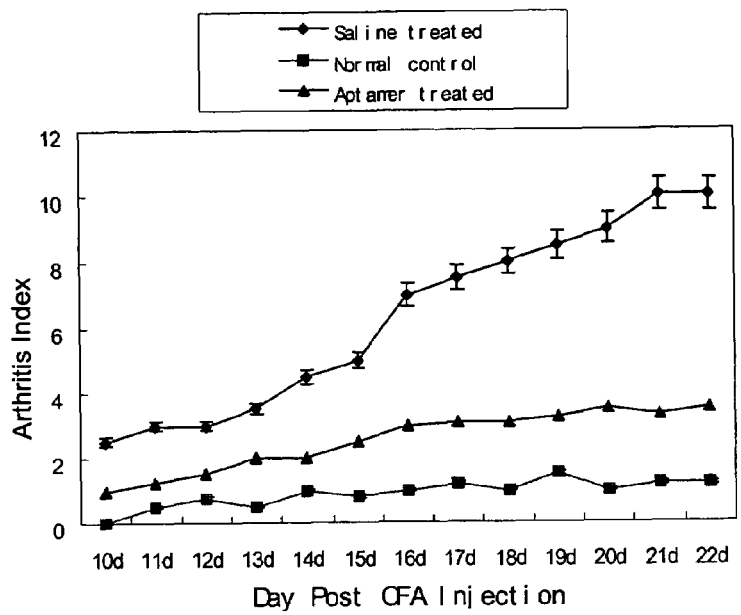
FIG. 13 shows arthritis index of a rat RA model treat with RNA SEQ No. 25 and the control (mean arthritis score±SEM)
Figure 14:
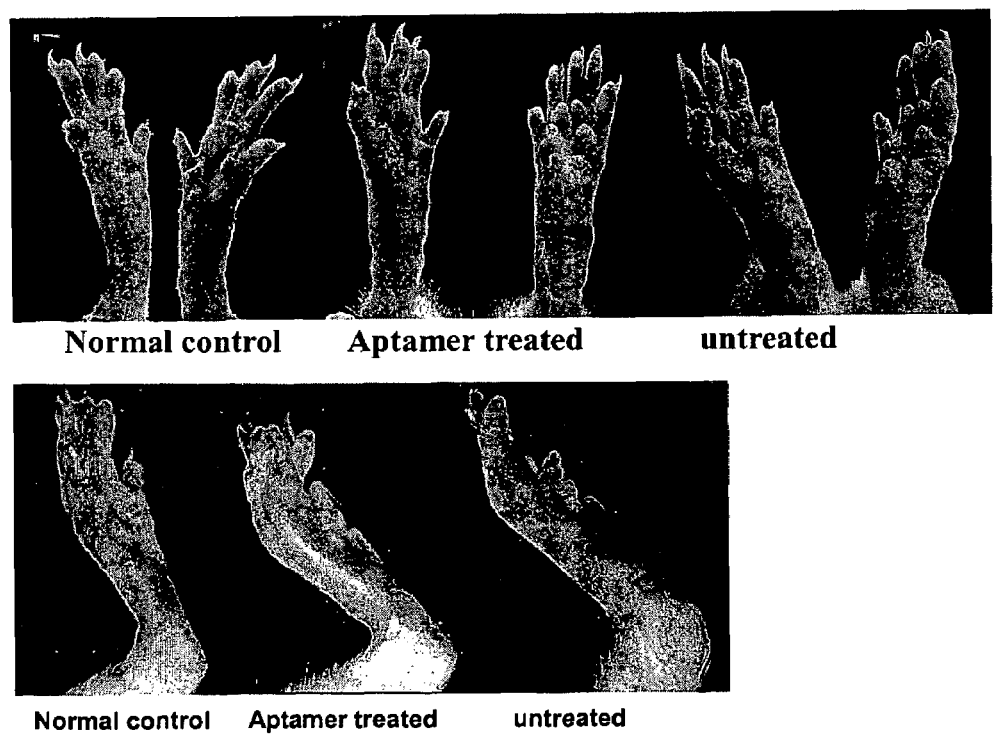
FIG. 14 shows representative photographs of hind limb from a normal rat, RNA SEQ No. 25-treated rat RA model and no-treatment rat RA model.

To determine the efficacy of TNF aptamers in vivo, the effects of modified aptamers SEQ No. 25 on the rat arthritis induced by complete Freund's adjuvant (CFA) were studied. Rats arthritis were induced with single intradermal injection of the CFA containing 1 mg of *Mycobacterium bovis* in the basis of the tail. The aptamer was injected intraperitoneally into rat (1 mg/kg) at days 0, 2, 4, 6, and 7-21 post-induction. Control rats received saline or yeast tRNA. Animals were daily scored for clinical signs of RA during period of 22 days. Arthritis was assessed using a scale from 0 to 16 (Griffiths, Eichwald, Martin, Smith & DeWitt, 1981), with each of four paws being scored from 0 to 4 as follows: 0=no arthritic changes; 1=edema and/or arthritic nodules on one finger; 2=edema and/or arthritic nodules on two fingers; 3=edema and/or arthritic nodules on three-four fingers; and 4=edema and arthritic nodules on all fingers. Severity was quantified by daily scoring each paw from 0 to 4 (0=normal and 4=maximum) based on increasing levels of swelling and periarticular erythema. The sum of the scores for four limbs was calculated as an arthritic index, with a maximum possible score of 16 per rat (front limbs and hind limbs). FIG. 13 shows the results. Experimental rats were treated with modified aptamer on alternate Days 0-22 after CFA injection. Severity of arthritis was significantly lower in aptamer treated rats from day 15 until the end of the study (P<0.001). Limb was photographed on day 22 post-CFA injection. FIG. 14 shows the photographs. Rats treated by aptamer had mild synovitis compared to severe disease in adjuvant arthritis rats control (P<0.001).

EXAMPLE 20

Pathology

Figure 15:
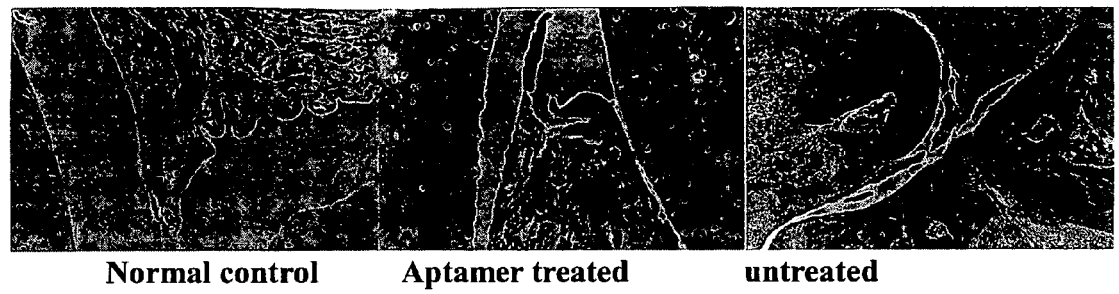
FIG. 15 shows pathology study of hind limb joints from a normal rat, RNA SEQ No. 25-treated rat RA model and no-treatment rat RA model.

All hind limbs were isolated on day 22. For histological analyses, the knee joints were dissected, fixed in a solution of 4% paraformaldehyde in a phosphate-buffered saline (PBS), and decalcified in a phosphate-buffered saline including 10% EDTA (pH 7.4). The samples were then dehydrated through an ethanol series and embedded in a paraffin block. Longitudinal sections through the entire foot/ankle were obtained and mounted on a L-polylysine-coated slide for further study. Each slide was stained with haematoxylin and eosin (H-E) for histological examination. FIG. 15 shows the result. Histologic sections of hind limb joints from adjuvant arthritis rats revealed the cell proliferation of synovium, multiplication of synovial lining cells, edema and pannus formation joint destruction, and neovascularization. The severe structural changes, such as the pannus invasion into the cartilage, the thickened trabecular bones, and the cellular aggregation in subchondral bone region of adjuvant-induced arthritis rat were evidently observed. All of these signs were absent or very mild in aptamer treated rat RA model and normal rats.

EXAMPLE 21

Evaluation of IFN-γ Producing Cells by Eli-Spot Assay

Figure 16:
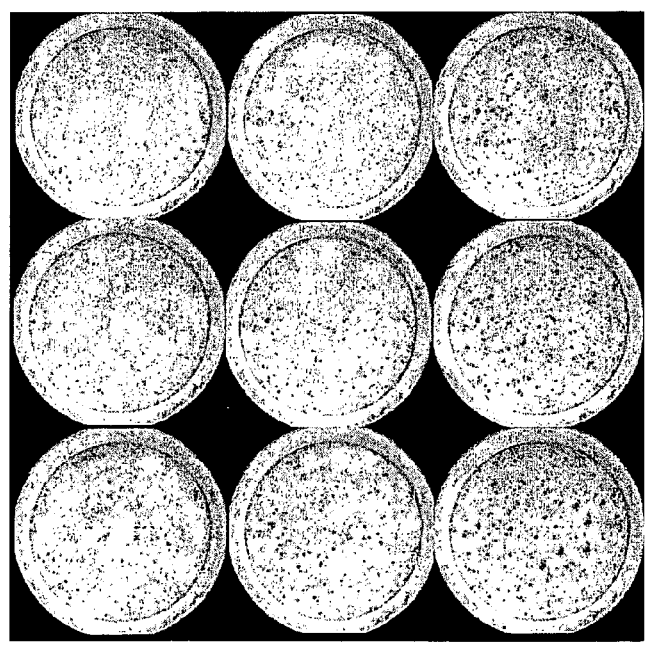
FIG. 16 shows detection of IFN-γ producing cells from a normal rat, RNA SEQ No. 25-treated rat and no-treatment rat RA model by Eli-spot assay.

Splenic mononuclear cells were obtained from normal rats, aptamer-treated rat RA model and untreated rat RA model. Splenocytes were purified by Ficoll-Hypaque (Pharmacia, Piscataway, N.J.) centrifugation and stimulated with PMA for IFN-γ production. Spleen cells are incubated in IFN-γ monoclonal antibody coated PVDF-bottomed-plate. After removal of the cells, bound IFNγ were revealed by a secondary biotinylated antibody, which was in turn recognized by streptavidin conjugated to alkaline phosphatase. PVDF-bottomed plate was then incubated with BCIP/NTB substrate. Purple color spots indicate cytokine production cells. FIG. 16 shows the result. The formation of purple spots are due to the IFN-γ secreted locally by individual spleen cells. Splenocytes from normal and aptamer-treated rat RA model produced fewer spots than those from untreated rat model.

The invention claimed is:

1. An oligonucleotide sequence that specifically binds to human tumor necrosis factor α (TNF-α), said oligonucleotide sequence being selected from SEQ ID NO.: 25.

2. The oligonucleotide sequence as claimed in claim 1, wherein the oligonucleotide sequence comprises a further truncated oligonucleotide sequence that functions identical to the oligonucleotide sequence of SEQ ID NO.: 25.

3. The oligonucleotide sequence as claimed in claim 1, wherein the oligonucleotide sequence has the following stem-loop structure:

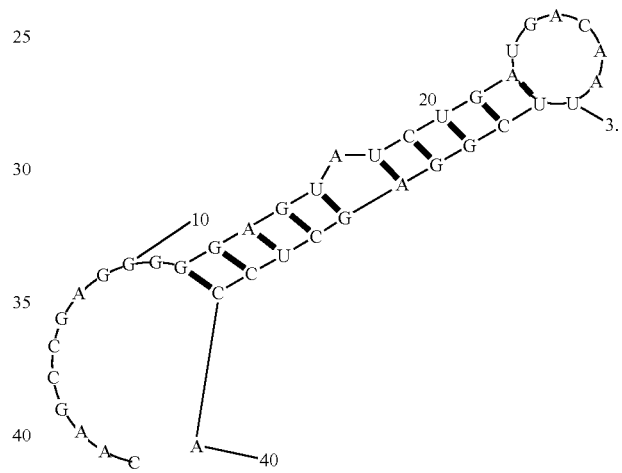

(SEQ ID NO: 25)

* * * * *

UNITED STATES PATENT AND TRADEMARK OFFICE
CERTIFICATE OF CORRECTION

PATENT NO. : 7,309,786 B2
APPLICATION NO. : 10/822761
DATED : December 18, 2007
INVENTOR(S) : Zhiqing Zhang et al.

It is certified that error appears in the above-identified patent and that said Letters Patent is hereby corrected as shown below:

On the title page, insert item:
(73) Assignee: Institute for Viral Disease Control and Prevention, Chinese Center for Disease Control and Prevention, Beijing, China Signed and Sealed this Fifteenth Day of July, 2008

JON W. DUDAS
*Director of the United States Patent and Trademark Office*